US00PP08920P

United States Patent [19]

Weeks

[11] Patent Number: Plant 8,920

[45] Date of Patent: Oct. 4, 1994

[54] HYBRID TEA ROSE PLANT NAMED 'LADY LAVENDAR'

[75] Inventor: O. L. Weeks, Chino, Calif.

[73] Assignee: Estrella Rose Company, Litchfield Park, Ariz.

[21] Appl. No.: 812,170

[22] Filed: Dec. 23, 1991

[51] Int. Cl.[5] ..... A01H 5/00
[52] U.S. Cl. ..... Plt./11
[58] Field of Search ..... Plt. 11, 18, 19

[56] References Cited

PUBLICATIONS

Modern Roses 8. "The International Check-List of Roses", The American Rose Society, 1980, p. 256.

*Primary Examiner*—Howard J. Locker
*Attorney, Agent, or Firm*—Joseph H. Roediger

[57] ABSTRACT

A new and distinct variety of Hybrid Tea rose Plant is provided having double flowers of original even mauve blend. The new variety is particularly suited for use in the beautification of parks and gardens.

1 Drawing Sheet

BACKGROUND OF THE NEW PLANT

The present invention relates to a new and distinct variety of rose plant of Hybrid Tea class which is distinguished from already known varieties in this class and color range. The new variety of rose plant was originated by me by crossing the variety Swarthmore, U.S. Plant Pat. No. 2,444, with the product of the pollination of the variety Paradise, U.S. Plant Pat. No. 4,552 and an unnamed seedling.

The present variety has an erect growth habit which is well organized and balanced. The plant has a double flower of original mauve blend never before realized that it is even in color and fade resistant. The plant tolerates heat conditions very well. Because of the above-mentioned characteristics, the present invention responds to the needs of the horticultural industry for all uses and, particularly, for park and garden decoration.

The new variety of rose plant owes its origin to an artificial pollination made between two parents by me in a greenhouse in Chino Calif. in 1983. The rose plant chosen as the seed parent was the product of the pollination of the patented variety Paradise by an unnamed seedling. The plant chosen as the pollen parent was the patented variety Swarthmore. The operation of artificial pollination thus made is expressed by the following: (Paradise × unnamed seedling) × Swarthmore.

The seeds resulting from the above-noted pollination were sown and small plants were obtained. These plants were both physically and biologically distinct from one another. After eliminating all the deficient or abnormal subjects whose characteristics deviated from those which were the object of the research, propagation of the remaining plants was undertaken. In the course of this study all the varieties were systematically eliminated, with the exception of the plant closest to the desired goal.

This rose plant produced double flowers of an original mauve blend color which did not fade. For exhibition purposes, the flowers showed a very nice shape with petals displaying an even color. Technical tests of asexual propagation by budding, grafting and cuttage were then undertaken in a greenhouse in Chino, Calif. with the aim of verifying the behavior and the productiveness of the created variety. The results were conclusive and stressed the importance of this variety with a view to its industrial exploitation for all uses and more importantly for park and garden decoration.

The characteristics and properties of the new variety obtained are stable and are transmissible by budding, grafting and cuttage. This new variety is called the Lady Lavendar variety of hybrid tea rose plant.

DESCRIPTION OF THE DRAWING

The accompanying drawing shows in colors as nearly true as it is reasonably possible to attain in color photographs of this nature: defoliated canes with thorns, terminal growth, the flower in various stages of maturity, detached petals and foliage of the new plant.

DESCRIPTION OF THE NEW VARIETY

The following descriptive characteristics of the new variety were taken from two (2) year old plants grown in container, budded in Chino, Calif. and observed in April in the green house.

The Pantone Library of Color, 1990 edition is used for the identification of the colors. The terminology which accompanies the numbered references proper to this chart has been added to qualify, in common terms, the corresponding colors.

THE PLANT

Class: Hybrid Tea.
Height: 40–42 I inches.
Habit: Upright.
Branches:
- *Young stems.*—Pantone 370, stained with reddish color.
- *Adult Wood.*—Pantone 371U, yellow green.
- *Thorns.*—Size: Large. Quantity: Moderately numerous. Color: Young stems: Pantone 367U, light green. Adult wood: Pantone 369U, dark green.
- *Stem length.*—14–17 inches.

Leaves:
- *Stipules.*—Adnate, pectinate, wide and dented.
- *Petioles.*—Color: Upper side: Young leaf — Pantone 382U, light green. Adult leaf — Pantone 368U, medium green. Under side: Pantone 382U, medium green, smooth.

*Leaflets.*—Number 5 and 7. Shape: Elliptic. Serration: Single and regular. Texture: Consistent. General effect: Dense, dark green. Color — young foliage: Upper side: Pantone 370U. Under side: Pantone 368U. Color — adult foliage: Upper side: Pantone 371U. Under side: Pantone 370U.

Inflorescence:

*Number of flowers.*—Usually 1 flower per stem.

*Peduncle.*—Length is 2½" on average.

*Sepals.*—Color: Upper side; greenish tomentose. Shape: Lanceolate with hairy edges, do not extend beyond bud. Number: Five, simple.

*Bud.*—Shape: Pointed. Length: 1⅛" on average. Size: Medium to large. Color: When opening: Upper side: Pantone 2563U. Under side: Pantone 256U.

Flower:

*Shape.*—When bloom first opens, cup-shaped with upright petals. When bloom matures, petals spread and curl back.

*Diameter.*—3½" to 4".

*Color.*—When blooming: Upper side: Pantone 250U. Under side: Pantone 2653U. When finishing blooming: Upper side: Pantone 263U. Under side: Pantone 263U.

*Fragrance.*—Moderate.

*Lasting quality.*—7 to 10 on the plant, 6 to 8 days when cut, clean petal drop.

*Petals.*—Color: Near point of attachment: Pantone 250U. At point of attachment: Pantone 251U. Shape: Generally orbicular. Texture: Consistent. Number: 33 on average. Cleaning: Good.

*Stamens.*—Number: Approx. 160. Anthers: Normal strawlike. Filaments: Regular in height, uniformly located around receptacle.

*Pistils.*—Number: About 45 outside — 50–60 bundled together inside as a group. Stigmas: Normal Style: Regular in height within each group; the inner pistils are smaller than the outer group.

*Receptacle.*—Medium green, smooth.

Development:

*Vegetation.*—Vigorous.

*Blooming.*—Continuous throughout seasons.

*Aptitude to bear fruits.*—Slight.

*Resistance to frost.*—Good.

*Resistance to disease.*—Normal.

I claim:

1. A new and distinct variety of Hybrid Tea rose plant substantially as described and shown herein.

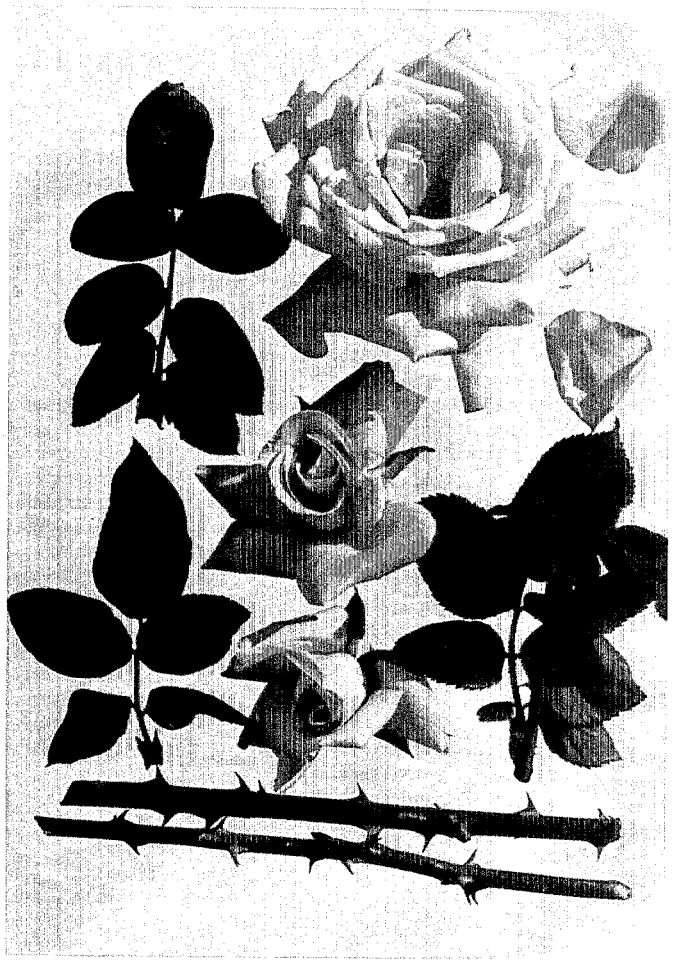

* * * * *